United States Patent [19]

Lord

[11] Patent Number: 5,407,642
[45] Date of Patent: Apr. 18, 1995

[54] CLIP MOUNT AIR FRESHENER ASSEMBLY

[76] Inventor: Paul J. Lord, 72 Hillcrest Ave., Wethersfield, Conn. 06109

[21] Appl. No.: 77,828

[22] Filed: Jun. 14, 1993

[51] Int. Cl.[6] ........................ A61L 9/00; A62B 7/08
[52] U.S. Cl. ........................ 422/122; 24/504; 239/55; 239/57; 422/1; 422/5; 422/120
[58] Field of Search ........................ 422/1, 5, 266, 120, 422/122; 239/55, 57, 327, 391–394; 24/489, 504, 511, 590, 453

[56] References Cited

U.S. PATENT DOCUMENTS

| | | | |
|---|---|---|---|
| 1,687,830 | 10/1928 | Clevenger | 239/57 X |
| 1,780,408 | 11/1930 | Smith . | |
| 2,091,420 | 8/1937 | Segal | 24/504 |
| 2,141,402 | 12/1938 | Muller . | |
| 2,237,731 | 4/1941 | Freysinger | 24/504 X |
| 2,251,058 | 7/1941 | Kirkman | 422/5 X |
| 2,560,681 | 7/1951 | Berkowitz . | |
| 2,670,990 | 3/1954 | Adair | 239/55 |
| 2,681,827 | 6/1954 | Racz | 239/57 |
| 3,784,102 | 1/1974 | Stults | 239/36 |
| 4,145,001 | 3/1979 | Weyenberg et al. | 239/56 |
| 4,178,346 | 12/1979 | Allen et al. | 422/126 |
| 4,277,863 | 7/1981 | Faneuf | 24/3 R |
| 4,383,377 | 5/1983 | Crafton | 34/60 |
| 4,523,870 | 6/1985 | Spector | 98/2.11 |
| 4,660,763 | 4/1987 | Coutkowski et al. | 239/43 |
| 4,662,039 | 5/1987 | Richardson | 24/489 |
| 4,813,344 | 3/1989 | Greif | 98/2.11 |
| 4,840,773 | 6/1989 | Wade | 422/124 |
| 4,849,606 | 7/1989 | Martens, III et al. | 219/271 |
| 5,004,138 | 4/1991 | Gabas | 239/55 X |
| 5,087,273 | 2/1992 | Ward | 422/5 X |
| 5,136,684 | 8/1992 | Lonker et al. | 392/392 |

FOREIGN PATENT DOCUMENTS 0307791 12/1991 France .

Primary Examiner—Robert J. Warden
Assistant Examiner—Krisanne M. Thornton

[57] ABSTRACT

A clip mount air freshener assembly has an air freshening element, and a holder providing a channel which slidably seats the air freshening element, and a spring mounting clip for mounting the air freshener assembly on the grill of a ventilator so that a stream of air issuing therefrom will flow over the exposed surface of the air freshening element. In the preferred embodiment, the holder and the clip are separate members, with each of the members providing pivot surfaces. A connector between the holder and the clip provides pivoting elements, pivotable on the pivot surfaces to provide pivotal motion of the holder in two orthogonal axes of rotation with respect to the spring mounting clip.

10 Claims, 3 Drawing Sheets

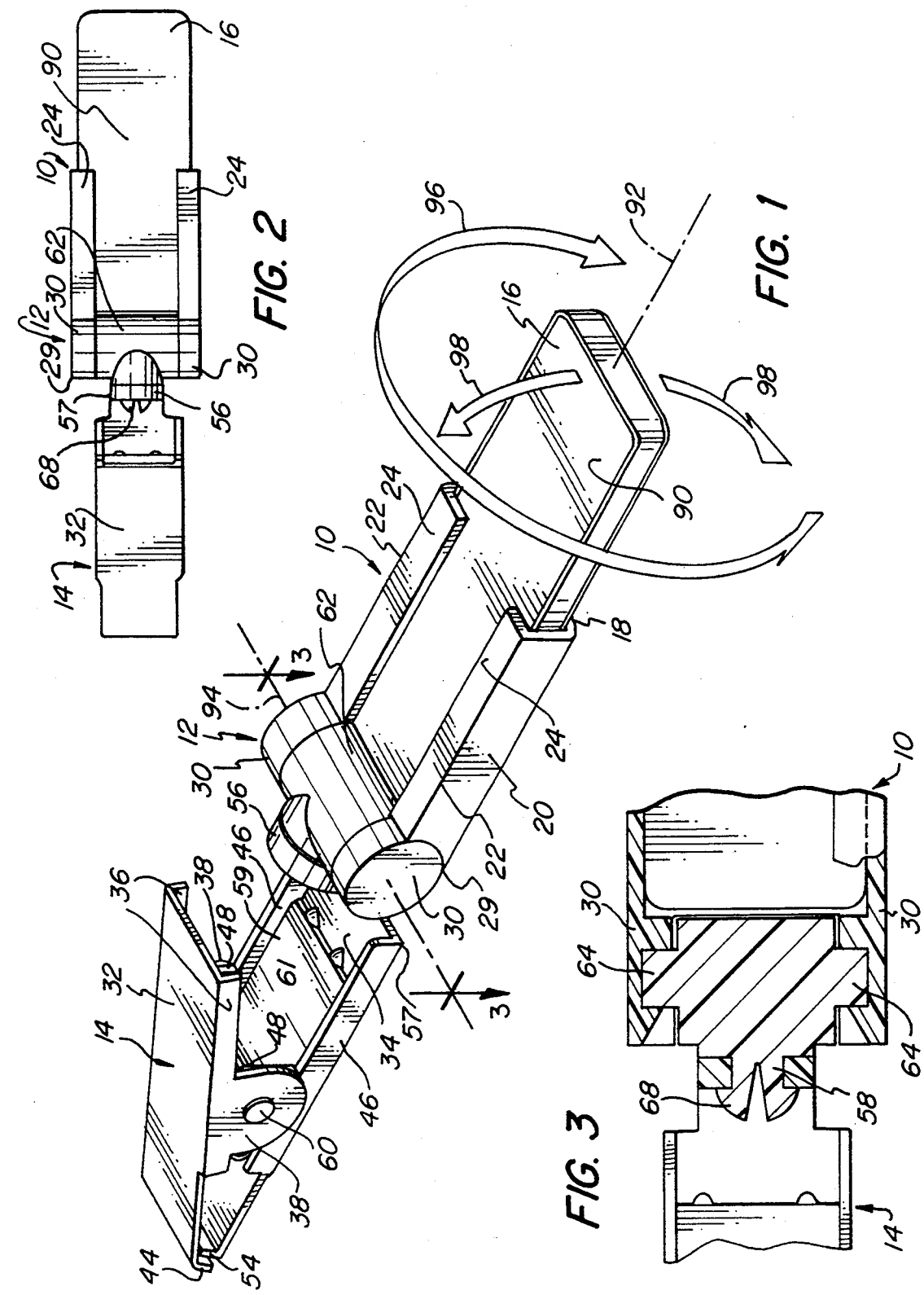

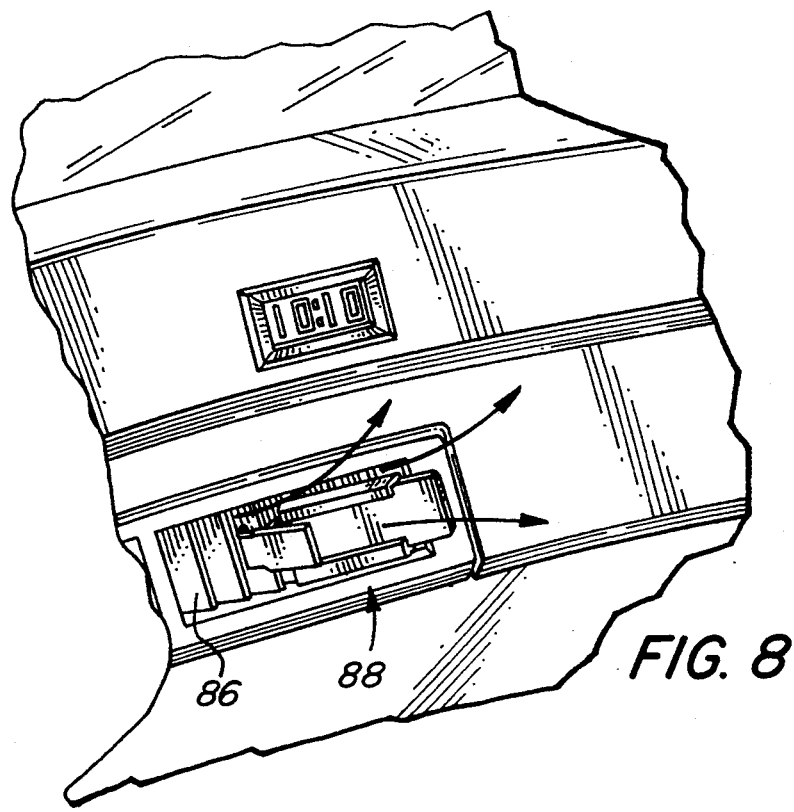
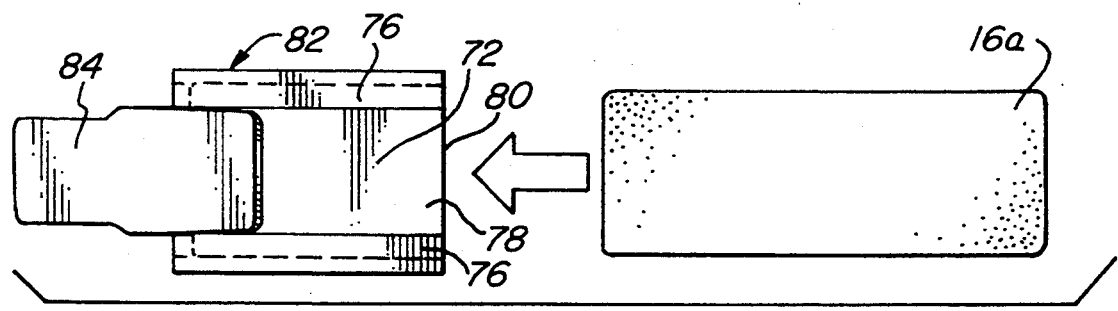
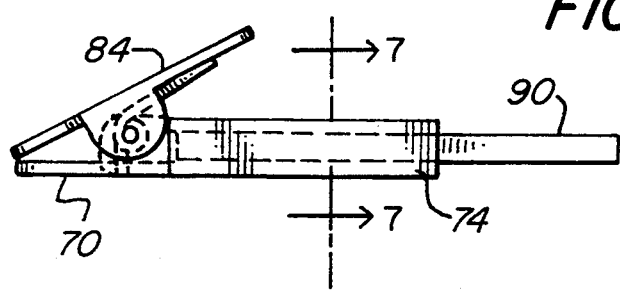
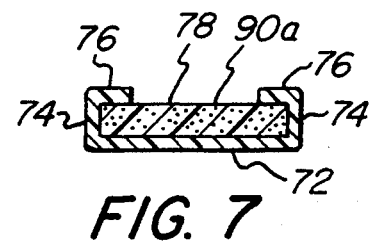

CLIP MOUNT AIR FRESHENER ASSEMBLY

BACKGROUND OF THE INVENTION

The present invention relates to air freshener assemblies and, more particularly, to clip mounted air freshener assemblies used on ventilation grills.

Air freshener assemblies of various types are well known in the art. They have typically been employed in such environments as a motor vehicle, the home, the office environment, and even in industry. In a motor vehicle, there is typically a concern about exhaust, road smells, and even tobacco smoke. In the home, one is often concerned with cooking odors, pet smells, or a general mustiness that can result from the house being sealed during inclement weather. Often, offices must deal with the need to freshen the air in smoking areas or cooking areas. The uses in industry are abundant.

Typically the air freshening material will take the form of a solid, liquid, or gel, with a liquid typically being adsorbed in a sponge or foam material.

Various embodiments of the prior art have sought to provide an air freshening assembly that is replenishable and controllable as to its consumption. Various prior art devices represent a trade-off among the desired features.

Grief U.S. Pat. No. 4,813,344 encloses a deodorant or deodorizer in the bottom of a device which is closed by gluing, bonding, etc. Clearly, there is no method for replenishing the deodorant, and the device is fastened by interlocking fiber strips to the face of a grill in an automobile. There is no method of pivoting or rotating the holder to optimize air flow over the deodorant.

Spector U.S. Pat. No. 4,523,870 has a replaceable cartridge, as well as an embodiment in which the cap of the cartridge is removable. In the latter, it is necessary to remove the pad and impregnate it with the air freshening material. It appears necessary to actually remove the entire unit from the ventilating system to conveniently accomplish this replenishment. Further, there is no provision for pivoting of the device within the air stream. Additionally, the size of the device appears to greatly restrict the passage of air into the passenger compartment.

Wade U.S. Pat. No. 4,840,773 provides a filling aperture on a vertical wall in the front of the air freshener unit. This structure appears to require the removal of the unit from the air vent prior to filling. Some pivoting of the unit is contemplated through a ball and socket assembly, but the size of the unit, and its proximity to the air vent grate, greatly restrict any potential movement. Furthermore, the size of the unit will likely affect the flow of air passing to the passenger compartment.

It is an object of the present invention to provide a novel clip mount air freshener assembly for use with a ventilation system in a motor vehicle, home, office environment, or factory to continuously diffuse into the air flowing thereover an air freshening substance.

It is also an object to provide such a clip mount air freshener assembly which is simple to operate and refill.

Still another object is to provide such a clip mount air freshener assembly which can be manufactured from relatively economical components.

Another object is the provision of such a clip mount air freshener assembly which has a pivoting capability, thereby allowing the user to locate the air freshening element at a desired angular position in the flow of air and maximize the efficiency of the air freshener assembly.

SUMMARY OF THE INVENTION

It has now been found that the foregoing and related objects may be readily attained in a clip mount air freshener assembly having an air freshening element and a holder providing a channel open at one end thereof and slidably seating the air freshening element. The element is removable and insertable into the channel through its open end. A spring mounting clip is provided at the other end of the holder and mounts the air freshener assembly on the grill of a ventilating device so that a stream of air issuing therefrom will flow over the exposed surface of the air freshening element.

In the preferred embodiment the holder has a base wall and upstanding side walls defining the channel, and inwardly extending lips at the upper portions of the side walls to retain the air freshening element in the channel. The air freshening element is rectangular and is of greater length than the channel so that it extends outwardly of the channel when seated within the holder.

In one embodiment, the holder and the spring mounting clip are separately fabricated members, and one of the members provides a pivot surface and the other of the members provides a pivoting element which is pivotable on the surface to provide relative pivotal movement.

In the preferred embodiment, the holder and the spring mounting clip are separately fabricated members, and one of the members provides a first pivot surface and the other of the members provides a second pivot surface. A connector is disposed therebetween and provides a first pivoting element and a second pivoting element, the first pivoting element being pivotable on the first pivot surface and the second pivoting element being pivotable on the second pivot surface. Desirably, the first pivot surface is provided by a pair of spaced bearing surfaces on one of the members adjacent the connector. The second pivot surface is provided by an aperture in the other of the members adjacent the connector. Usually, the first pivoting element of the connector comprises a pair of shafts seating on the bearing surfaces of the first pivot surface, and the second pivoting element comprise a pin extending into the aperture providing the second pivot surface. The connector has a generally cylindrical body with the shafts extending axially from its ends and the pin extending radially therefrom. In this preferred embodiment, the holder is rotatable along at least two orthogonal axes of rotation with respect to the spring mounting clip.

BRIEF DESCRIPTION OF THE DRAWINGS

FIG. 1 is a perspective view of a clip mount air freshener assembly embodying the present invention, with the arrows showing the directions of pivotal motion;

FIG. 2 is a top plan view of the clip mount air freshener assembly of FIG. 1;

FIG. 3 is a fragmentary cross sectional view, in enlarged scale, of the clip mount air freshener assembly along the line 3—3 of FIG. 1, and with part of the holder broken away;

FIG. 5 is a side elevational view of a second embodiment of the clip mount air freshener assembly of the present invention;

FIG. 6 is a top plan view of the clip mount air freshener assembly of FIG. 5, showing an air freshening element removed from the assembly and with an arrow indicating the direction of insertion;

FIG. 7 is a vertical cross sectional view of the clip mount air freshener assembly along the line 7—7 of FIG. 5; and FIG. 8 is a perspective view of the clip mount air freshener assembly of FIG. 5, as mounted on the grill of a motor vehicle ventilator.

DETAILED DESCRIPTION OF THE PREFERRED EMBODIMENT

Figure 4:
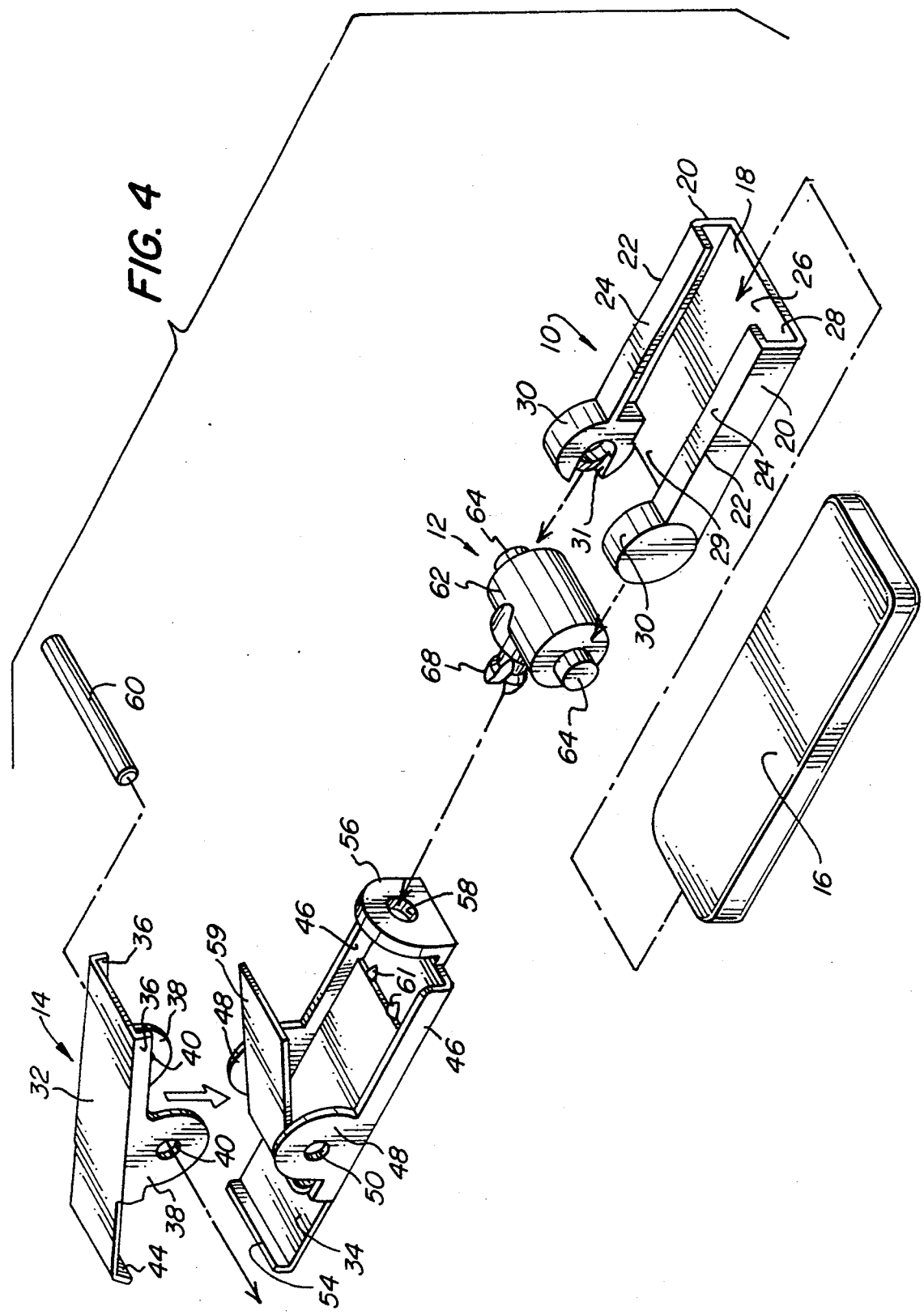
FIG. 4 is an exploded view of the clip mount air freshener assembly of FIG. 1.

Referring first to FIGS. 1–4, there is shown a preferred embodiment of a clip mount air freshener assembly embodying the principles of the present invention and having a holder generally designated by the numeral 10, a connector generally designated by the numeral 12, a spring mounting clip generally designated by the numeral 14, and an air freshening element 16.

The holder 10 has a base wall 18 and upstanding side walls 20, and the upper portions 22 of the side walls 20 are inwardly extending lips 24. The base wall 18 and side walls 20 serve to form a channel 26 in the holder 10, and the lips 24 act to retain the air freshening element 16 in the channel 26 allowing the holder 10 to slidably seat the air freshening element 16. The channel 26 is open at one end 28 of the holder 10, and the air freshening element 16 is removable and insertable into the channel 26 through this open end. As can be seen, the air freshening element 16 is of greater length than the channel 26 so that the air freshening element 16 extends outwardly of the channel 26 when seated within the holder 10. At the other end 29 of the holder 10 are two spaced journal bearings 30 having bearing surfaces 31 and providing a first pivot surface.

The spring mounting clip 14 has an upper jaw 32 and a lower jaw 34, respectively having side walls 36, 46 extending along portions of the length thereof and towards each other. Extending from the sidewalls 36, 46 in overlying relationship are the ears 38, 48, respectively which have aligned apertures 40 and 50, respectively therein.

The upper jaw 32 has a clamping lip 44 depending from its front end, and the lower jaw 34 has an upstanding clamping lip 54 at its front end.

At its rear end, the lower jaw 34 has a transversely oriented upstanding wall 56 with an aperture 58 providing a second pivot surface.

In a variation of this embodiment, the spring mounting clip 14 can provide the bearing surfaces 31 of the journal bearings 30, with the holder 10 providing the wall 56 with an aperture 58.

The spring mounting clip 14 is assembled in the conventional manner. A leaf spring 59 is inserted between the upper jaw 32 and the lower jaw 34. The apertures 40 on the ears 38 of the upper jaw 32 are aligned with the apertures 50 on the ears 48 of the lower jaw 34. Once they are aligned, a pivot pin 60 is inserted through the apertures 40 and 50. Pairs of bosses 61 on both the upper jaw 32 and the lower jaw 34 act to retain the leaf spring 59 in proper position.

The connector 12, located between the holder 10 and the spring mounting clip 14, is comprised of a generally cylindrical body 62 having two stub shafts 64 extending axially from the ends of the body 62 providing a first pivoting element which seats in the journal bearings 30. A pin 68 extends radially from the body 62 toward the clip 14, and provides a second pivoting element seating in the second pivot aperture 58.

The air freshening element 16 can take numerous forms. In one form, it is a rectangular piece of sponge or foam material impregnated with an air freshening liquid such as a deodorizer or perfume. In another form, the air freshening element can be a rectangular planar piece of paperboard, similarly impregnated with an air freshening liquid. In still another form, it can be a rectangular piece of solid or semi-solid air freshening material. The air freshening material in this latter instance may be supported in a frame.

In this preferred embodiment, the holder 10 and the spring mounting clip 14 are separately fabricated members. Further, the holder 10 is rotatable along at least two orthogonal axes of rotation, 92 and 94, with respect to the spring mounting clip 14.

Referring to FIG. 1, rotation along the axis of rotation 92, provides for movement of the holder 10 in the direction of the double-headed arrow 96. Rotation along the axis 94 provides for movement of the holder 10 in the direction of the arrows 98.

The clip mount air freshener assembly is assembled by extending the pin 68 into the aperture 58 of the aperture wall 56, in which it is pivotable. The stub shafts 64 are seated in the bearing surfaces 31 of the journal bearings 30, on which they are pivotable.

The air freshening element 16 is then inserted into the holder 10 through the open end 28 of the holder 10 and extends outwardly therefrom. In this manner, there is ample exposed surface 90 of the air freshening element 16.

By pivoting the pin 68 in the aperture 58 and by pivoting the shafts 64 in the journal bearings 30, the holder 10, and thereby the air freshening element 16, can be pivoted in two separate axes of rotation 92 and 94, and in the direction of the arrows 96 and 98, respectively. This allows optimal positioning of the air freshening element 16 in the airstream.

Referring to FIGS. 5–8, there is shown an alternate embodiment of the clip mount air freshening assembly. In this embodiment, the lower jaw 70 of the clip and the base wall 72 of the holder are a continuous planar portion.

The base wall 72 has upstanding side walls 74 along a portion of its length with inwardly extending lips 76 at the upper portions thereof. The base wall 72 and side walls 74 similarly form a channel 78 with an open end 80, and the lips 76 act to retain the air freshening element 16a in the channel 78.

The base wall 72, side walls 74 and lips 76 form a holder section generally indicated as 82.

An upper jaw 84 is pivotably supported on the pivot pin 60a and is biased relative to the lower jaw 70 by the leaf spring 59a in a manner similar to the preferred embodiment.

Referring to FIG. 8, it can be seen that the clip mount air freshener assembly is attached to a grill 86 of an associated ventilator 88 so that a stream of air from the ventilator 88 will flow over the exposed surface 90 or 90a of the air freshening element 16 or 16a. The effect of the air freshening element 16 or 16a can be maximized or rejuvenated by increasing the temperature of the airstream passing over the air freshening element 16 or 16a, if such a capability is provided by the ventilator 88. Additionally, once the exposed surface 90 or 90a of the air freshening element 16 is depleted of the air freshening component, the exposed surface 90 or 90a can be changed by merely inverting the air freshening element 16 or 16a in the holder 10 or 10a.

In addition to the ventilating system of a motor vehicle, the ventilator 88 may be a fan in an office, home or industrial environment, or other such ventilating system.

In addition, it will be appreciated that the preferred embodiment permits pivoting of the holder to orient the freshening element in the air stream.

Another embodiment can be visualized by reference to FIG. 1, but the connector 12 is integral with holder 10. There are no shafts 64 and bearing surfaces 31 to rotate. The pin 68 is pivotable, however, in the aperture 58, allowing rotation about the axis 92.

A variant of this embodiment forms the connector integrally with the lower jaw 34 of the spring mounting clip 14. In this variant, there is no pin 68 or aperture 58, and the stub shafts 64 are pivotable on the bearing surfaces 31. This capability allows the holder 10 to pivot with respect to the spring mounting clip 14 along the axis 94.

Referring to FIGS. 1, 2, 5 and 6, it can be seen that the holder 10, connector 12, spring mounting clip 14 and air freshening element 16, all have various contiguous surfaces. These surfaces can be utilized to carry printed matter for marketing or advertising purposes, thereby augmenting the uses to which the clip mount air freshener assembly can be put.

The clip mount air freshener assembly, whether in the preferred embodiment or one of the alternate embodiments, may be fabricated from metal, polymers, wood, or other suitable material. Similarly, combinations of these materials may be employed. Molding the elements from synthetic resin is simple and economical. With any of these materials, the holder can perforate, thereby increasing the exposed surface 90 or 90a of the air freshening element 16.

Thus, it can be seen from the foregoing detailed specification and attached drawings that the novel clip mount air freshener assembly of the present invention may be installed readily in the ventilation system of a motor vehicle, home, office environment, or factory to continuously diffuse an air freshening substance which can be readily replenished. The assembly can be manufactured from relatively economical components to provide a long lived structure. Additionally, the assembly has a pivoting capability, allowing for location of the air freshening element at a desired angular position in the flow of air.

Having thus described the invention, what is claimed is:

1. A clip mount air freshener assembly comprising:
   (a) a substantially planar air freshening element comprising a body of substantially uniform thickness containing a diffusible air freshening material;
   (b) a holder having a base wall and opposed upstanding side walls with inwardly extending lips at the upper portions thereof and providing a channel entirely open over its length but for the lips, said holder being open at one end thereof and slidably seating said air freshening element, said element being removable and insertable into said channel through said open end thereof without dissassembly of said holder and said lips retaining said air freshening element in said channel, the major portion of the outer surface of said element being exposed to the atmosphere; and
   (c) a spring mounting clip extending outwardly from the other end of said holder and having a pair of jaws orientable in substantially axial alignment with said channel, whereby said air freshener assembly may be mounted on the grill of an associated ventilating device so that a stream of air issuing therefrom will flow over said exposed surface of said air freshening element.

2. The clip mount air freshener assembly of claim 1 wherein said air freshening element is rectangular and is of greater length than said channel so that it extends outwardly of said channel when seated within said holder.

3. The clip mount air freshener assembly of claim 1 wherein said holder and said spring mounting clip are separate members and wherein one of said members provides a pivot surface and the other of said members provides a pivoting element which is pivotable on said surface to provide relative pivotal movement therebetween about an axis extending longitudinally of said holder and clip.

4. The clip mount air freshener assembly of claim 1 wherein said holder and said spring mounting clip are separate members, and wherein one of said members provides a first pivot surface and the other of said members provides a second pivot surface, said assembly including a connector therebetween providing a first pivoting element and a second pivoting element, said first pivoting element being pivotable on said first pivot surface and said second pivoting element being pivotable on said second pivot surface, said holder thereby being rotatable along at least two orthogonal axes of rotation with respect to said spring mounting clip.

5. The clip mount air freshener assembly of claim 4 wherein said first pivot surface is provided by a pair of spaced bearing surfaces on one of said members adjacent said connector, said second pivot surface is provided by an aperture in the other of said members adjacent said connector, and wherein said first pivoting element of said connector comprises a pair of shafts seating on said bearing surfaces of said first pivot surface, and said second pivoting element comprises a pin extending into said aperture providing said second pivot surface.

6. The clip mount air freshener assembly of claim 5 wherein said connector has a generally cylindrical body with said shafts extending axially from its ends and said pin extending radially therefrom.

7. The clip mount air freshener assembly of claim 1 wherein said holder is rotatable along at least two orthogonal axes of rotation with respect to said spring mounting clip.

8. A clip mount air freshener assembly comprising:
   (a) a substantially planar air freshening element comprising a body containing a diffusible air freshening material;
   (b) a holder having a base wall and opposed upstanding sidewalls with inwardly extending lips at the upper portions thereof and providing a channel substantially open over its length, said holder being open at one end and said channel seating said air freshening element for passage of air over a substantial portion of the surface thereof, said freshening element being insertable into and removable from said channel through said open end thereof without disassembly of said holder and said lips retaining said element in said channel;

(c) a spring mounting clip having a pair of jaws for mounting said air freshener assembly on the grill of an associated ventilating device; and (d) a connector connecting the other end of said holder and said clip with said jaws being spaced from said holder and orientable in substantially axial alignment with said channel, one of said clip and holder providing a first pivot surface and the other of said clip and holder providing a second pivot surface, said connector having a first pivoting element pivotable on said first pivot surface and a second pivoting element pivotable on said second pivot surface, said holder thereby being rotatable along at least two orthogonal axes of rotation with respect to said spring mounting clip.

9. The clip mount air freshener assembly of claim 8 wherein said first pivot surface is provided by a pair of spaced bearing surfaces on one of said members adjacent said connector, said second pivot surface is provided by an aperture in the other of said members adjacent said connector, and wherein said first pivoting element of said connector comprises a pair of shafts seating on said bearing surfaces of said first pivot surface, and said second pivoting element comprises a pin extending into said aperture providing said second pivot surface.

10. The clip mount air freshener assembly of claim 9 wherein said connector has a generally cylindrical body with said shafts extending axially from its ends and said pin extending radially therefrom.

* * * * *